(12) United States Patent
Alexandre et al.

(10) Patent No.: US 6,913,593 B1
(45) Date of Patent: Jul. 5, 2005

(54) NEEDLELESS SYRINGE WHICH FUNCTIONS WITH THE ACTIVE AGENT BEING DRIVEN BY A SHOCKTUBE EFFECT

(75) Inventors: Patrick Alexandre, Gray (FR); Guy Delannoy, Saint Medard en Jalles (FR); Philippe Gautier, Le Plessis Pate (FR); Denis Roller, La Ferte Alais (FR)

(73) Assignee: Crossject, Paris (FR)

( * ) Notice: Subject to any disclaimer, the term of this patent is extended or adjusted under 35 U.S.C. 154(b) by 427 days.

(21) Appl. No.: 10/129,555

(22) PCT Filed: Nov. 23, 2000

(86) PCT No.: PCT/FR00/03256

§ 371 (c)(1),
(2), (4) Date: May 8, 2002

(87) PCT Pub. No.: WO01/41839

PCT Pub. Date: Jun. 14, 2001

(30) Foreign Application Priority Data

Dec. 8, 1999 (FR) .................................. 99 15473

(51) Int. Cl.[7] .............................................. A61M 5/30
(52) U.S. Cl. ............................. 604/69; 604/68; 604/48
(58) Field of Search ............................. 604/19, 22, 23, 604/24, 48, 57, 68–72, 82–88, 131, 140, 604/141, 145, 148

(56) References Cited

U.S. PATENT DOCUMENTS

| 2,322,244 A | | 6/1943 | Lockhart |
| 4,089,334 A | * | 5/1978 | Schwebel et al. ............. 604/69 |
| 5,899,880 A | * | 5/1999 | Bellhouse et al. ............ 604/70 |

FOREIGN PATENT DOCUMENTS

| EP | 0 755 689 A1 | 1/1997 |
| EP | 0 821 195 A2 | 1/1998 |
| WO | WO 94/24263 | 10/1994 |

* cited by examiner

Primary Examiner—Nicholas D. Lucchesi
Assistant Examiner—Jennifer J Maynard
(74) Attorney, Agent, or Firm—Oliff & Berridge, PLC

(57) ABSTRACT

The invention relates to a needleless syringe (1), comprising the following' successively: a gas generator, a gas expansion chamber (3), a means for retaining particles of the active agent and a tube (6) for ejecting said particles. The main characteristic of the inventive syringe is that the gas generator is a pyrotechnic generator (2), comprising a pyrotechnic charge (10) which generates gas, a gas generator and an initiation device. The invention is also characterized in that the retaining means comprise at least one lid (8), which is fixed to the ejection tube and is configured to break under the influence of the gases generated by the combustion of said charge (10).

20 Claims, 2 Drawing Sheets

NEEDLELESS SYRINGE WHICH FUNCTIONS WITH THE ACTIVE AGENT BEING DRIVEN BY A SHOCKTUBE EFFECT

The technical field of the invention is that of needleless syringes used for the subcutaneous or intramuscular injection of various active principles in pulverulent form or in the form of dry powders for therapeutic use in human or veterinary medicine.

More specifically, the invention relates to a needleless syringe using a gas generator which is intended to create a pressure wave for ejecting the particles of active principle. A burstable protective seal, placed on the pathway of the gases, makes it possible to obtain the threshold pressure level permitting ejection of the particles at a sufficiently high speed. This is because the sudden release of the gases creates a thermodynamic shock in the syringe and it is the shock wave which will carry and accelerate the particles in order to expel them from the syringe. The specificity of the invention lies in the fact that the needleless syringe functions with a pyrotechnic charge as the thermodynamic energy source for expelling the solid particles, this pyrotechnic charge being closely associated with the geometry of the ejection tube and its size.

The needleless syringes which function by release of a compressed gas in order to expel solid particles of active principle have already been the subject of several patents. Mention may be made, in particular, of patent application WO 94/24263 which describes a needleless syringe functioning by release of a reserve of gas in order to entrain the solid particles of active principle which are initially placed between two burstable transverse membranes positioned in the tube for ejection of the particles, but such a bulky device poses difficulties in terms of development and it is difficult to create an effective shock wave with it, because no thermal effect can be combined with the pressure of the gases.

By contrast, needleless syringes with a pyrotechnic charge for expelling an active principle have already been developed, but only for liquid active principles, not for active principles in powder form, and no shock-tube effect is produced because the gases only displace a piston acting on the liquid to be expelled.

By way of example, the patent U.S. Pat. No. 2,322,244 describes a needleless hypodermic injector functioning on the basis of a blank cartridge whose firing is triggered by the percussion of a piston moved at speed by the release of a spring. The liquid to be injected, placed in contact with the cartridge, is expelled from the injector under the effect of the pressure generated by the combustion gases.

The patent U.S. Pat. No. 4,089,334, for its part, relates to a needleless injector equipped with a pyrotechnic charge whose firing is ensured by a primary charge, itself initiated by percussion of a rigid rod set in motion by the release of a spring. The gases emitted by the pyrotechnic charge expand in a downstream chamber, setting in motion a piston whose displacement causes the expulsion of the liquid product to be injected.

As these two patents relate to needleless injectors intended to expel active principle in liquid form, the gases emitted by the pyrotechnic charge only have a thrust function similar to that of a piston. At no point do these patents advance the idea of creating a shock wave to accelerate solid particles.

Needleless syringes in general must not be too large and they must be effective, reliable and able to be easily adapted to the case to be treated, for example in terms of depth of penetration of the particles of active principle. These demands can be satisfied by using high-energy pyrotechnic charges in a needleless syringe together with a calibrated protective seal. This is because, compared to a conventional reserve of compressed gas, a pyrotechnic charge will be able to produce a very high level of pressure in the syringe within a very short time, these being the two conditions required to produce a shock wave, and it has been found that, on the one hand because of the release of the pyrotechnic gases at an initial high temperature, and on the other hand because of the very short time of contact between these gases and the active principle, and between these gases and the skin area to be injected, there is no problem in using a pyrotechnic charge to generate gases.

The shock wave is characterized mainly by its brevity, its very high intensity, and its very high speed of displacement, these being motor characteristics which are particularly suitable for injecting solid particles at very high speed, of the order of 800 m/s. Moreover, since pyrotechnic charges can be fired in a perfectly controlled manner with initiation devices which have been widely tried and tested, for example those possibly including a primary charge or a primer, the needleless syringes according to the invention have a very high degree of reliability as regards their motor function.

Another point to be underlined concerning the advantages linked with the use of a pyrotechnic charge relates to the great variability of the compositions which can be integrated in the device for triggering the syringe, thereby making it possible to adjust the motor parameters of said syringe to the case to be treated. Finally, in their storage phase, the needleless syringes according to the invention are not pressurized in the way that those functioning with a reserve of compressed gas may be, and this makes it possible, on the one hand, to significantly reduce the risks of incidents and, on the other hand, to ensure great stability of the motor function of the syringe over the course of time.

The needleless syringes according to the invention possess all of these characteristics.

The subject of the present invention is a needleless syringe comprising, in succession, a gas generator, a gas expansion chamber, a means for retention of the particles of an active principle, and a tube for ejection of said particles, characterized in that the gas generator is a pyrotechnic generator comprising a pyrotechnic charge which generates gas, and an initiation device, and in that the retention means comprises at least one protective seal which is fixed to the ejection tube and is intended to burst under the effect of the gases produced by the combustion of said charge. The phenomenon which is sought by using a pyrotechnic charge is the creation of a shock wave in order to carry the solid particles of active principle and expel them at a sufficient speed toward the skin of the patient to be treated. The shock wave is the result of the very rapid pressurization of the gases in a constant volume represented by the expansion chamber and of the bursting of a calibrated protective seal which causes the almost instantaneous release of the gases. The geometry, intensity and speed of the shock wave thus produced are a function of the characteristics of the pyrotechnic charge used, the shape and volume of the expansion chamber, and the shape and dimensions of the ejection tube. The pyrotechnic charge is preferably a low-oxygenation propellant for which live combustion produces what are called "cold" gases and whose temperature is below 1900 K, for example propellants based on sodium nitride or ammonium nitrate. More generally, the propellant has a nonhydrocarbonated and highly nitrogenous composition or an oxygenated hydrocarbonated composition.

Structurally, the propellant can either be in the form of a compact block or in a divided form. It is also possible to choose a powder whose controlled quasi-deflagration will allow the same characteristics to be obtained.

In fact, the effects generated by the combustion of a powder or of a propellant are summed up in particular in the production of gases, these being characterized essentially by their composition, their temperature and the pressure at which they are emitted. It is therefore desirable to choose pyrotechnic compositions whose combustion will neither directly alter the particles of active principle retained in the syringe nor pose any source of danger for the patient who is to be treated, but it is still possible to interpose a cooler of the heat sink type between the pyrotechnic charge generating gas and the active principle, which heat sink can, for example, consist of spherules of alumina disposed in a filter formed by fine metal grilles. It is for these reasons that the pyrotechnic charges retained must produce relatively non-toxic gases having a relatively low temperature. However, it should be noted that the temperature of the gases must not be considered as the decisive parameter in terms of the danger presented by the syringe to the patient to be treated, since the gases are emitted over a very brief time of the order of a few milliseconds, invalidating the aggression of the thermal fluxes on the patient's skin.

The protective seal is advantageously calibrated to yield at a dynamic pressure in the chamber of at least 70 bar and preferably a dynamic pressure of between 80 bar and 200 bar. The expansion chamber preferably comprises a filter having the twin function of holding back the undesirable particles issuing from the combustion gases and also of cooling said gases. The maximum temperature reached in the expansion chamber is advantageously between 350 K and 1500 K. The ejection tube is preferably a straight cylinder.

According to a first preferred embodiment of the invention, the gas expansion chamber is substantially cylindrical and its internal diameter is close to that of the ejection tube. The ratio of the sum of the lengths of the chamber and of the tube to their diameter is advantageously between 3 and 25, and preferably between 7 and 18.

According to a second preferred embodiment of the invention, the expansion chamber has a substantially cylindrical shape continued via a zone of narrowing which opens into the ejection tube, such that the internal diameter of said tube is smaller than the internal diameter of the cylindrical part of said chamber and the protective seal is fixed in the ejection tube of reduced diameter.

The zone of narrowing is preferably progressive, having a convergent nozzle shape. In fact, the change from a configuration, where the diameters of the chamber and of the tube are identical, to a configuration, for which the diameter of the tube is smaller than that of the chamber, is always accompanied by an increase in the speeds of ejection of the particles of active principle, and this for one and the same pyrotechnic charge. The ratio of the diameter of the cylindrical part of the expansion chamber to the internal diameter of the ejection tube is advantageously between 1.1 and 3, and preferably between 1.3 and 2.5.

The downstream segment of the tube, through which the particles are ejected, advantageously has a divergent conical part continued by a straight cylindrical part whose free end comes into contact with the skin. In this way, this divergent part makes it possible to increase the vent surface and thus to decrease the pressure at the outlet of the syringe without reducing the speed of ejection of the particles.

According to one or other of the two above preferred embodiments of the invention, the ratio of the length of the tube to the length of the chamber is between 1 and 5 and the sum of these two lengths is between 8 cm and 15 cm. The length of the chamber is preferably 3.5 cm and that of the tube 8.5 cm.

The diameter of the particles of active principle is advantageously between 20 $\mu$m and 100 $\mu$m, and preferably between 50 $\mu$m and 80 $\mu$m, and the total mass of said active principle is between 1 mg and 10 mg, and preferably between 2 mg and 7 mg. The particles are advantageously lodged between the protective seal and a membrane placed downstream of said protective seal in relation to the direction of propagation of the gases. Said membrane is preferably fine, nonelastic and transversal in relation to the axis of the tube. The compaction of the particles is advantageously between 1% and 70%, preferably between 10% and 50%. The compaction is defined as being the ratio of the total volume of the particles to the total volume of the ejection tube between the protective seal and the membrane.

The density of the particles of active principle is preferably between 1 and 22, preferably between 3 and 18. Indeed, it is the combination of the two parameters of "diameter of the particles" and "density of the particles" which will define their speed of ejection. In theory, the speed of the particles is inversely proportional to the density and the square of the diameter. It has been demonstrated by means of calculation that particles of small diameter can have high densities without thereby significantly affecting their speed. By contrast, if the particles are of a large size while at the same time having a high density too, the risk to be feared is that the shock wave issuing from the protective seal, which tears, will traverse these particles with high inertia and without actually entraining them along their complete course, the major consequence of which is a deceleration of the particles in relation to the entrainment gases and, ultimately, a speed of impact on the skin that is too slow to permit their penetration.

Advantageously, the ratio of the mass of the pyrotechnic charge to the mass of active principle to be ejected is between 1 and 50, and preferably between 5 and 40. According to another preferred embodiment of the invention, the means for retention of the particles comprises a transverse grille which is fixed to the ejection tube and on which said particles are maintained, these particles being able to be ejected under the effect of the pressure of the gases generated by the combustion of the pyrotechnic charge. This grille remains fixed to the inside of the syringe after the passage of the shock wave and thus avoids any risk of undesirable projections caused by rupturing of material.

The device for initiation of the pyrotechnic charge advantageously comprises a percussion device and a primer currently used in the pyrotechnics industry. However, it is also possible to initiate the pyrotechnic charge by other means, in particular those involving either a piezoelectric crystal or a roughening, or even a battery. It will be noted that a roughening is a small roughened area on which a friction-sensitive element can rub in a pyrotechnic device.

The syringe preferably has a trigger in the form of a push button placed at one of its ends in order to make it easier to grip and operate.

The needleless syringes according to the invention benefit from the advantages associated with functioning by means of a shock wave, in particular in terms of the speed of ejection of the particles, while at the same time ensuring reliable containment of the particles in storage mode.

Moreover, compared to a conventional compressed gas source, a pyrotechnic charge produces effects which are at least as intense, especially in terms of pressure, while at the same time being much smaller.

Moreover, the firing of the pyrotechnic charges, irrespective of their nature and their size, is perfectly controlled by using initiators which have been widely tried and tested, thereby rendering the drive part of the syringe very reliable and inexpensive.

Finally, the needleless syringes according to the invention are optimized in terms of performance as a result of a judicious geometry of the ejection tube.

Three preferred embodiments of the invention are described in detail below with reference to FIGS. 1 to 3.

Figure 1:
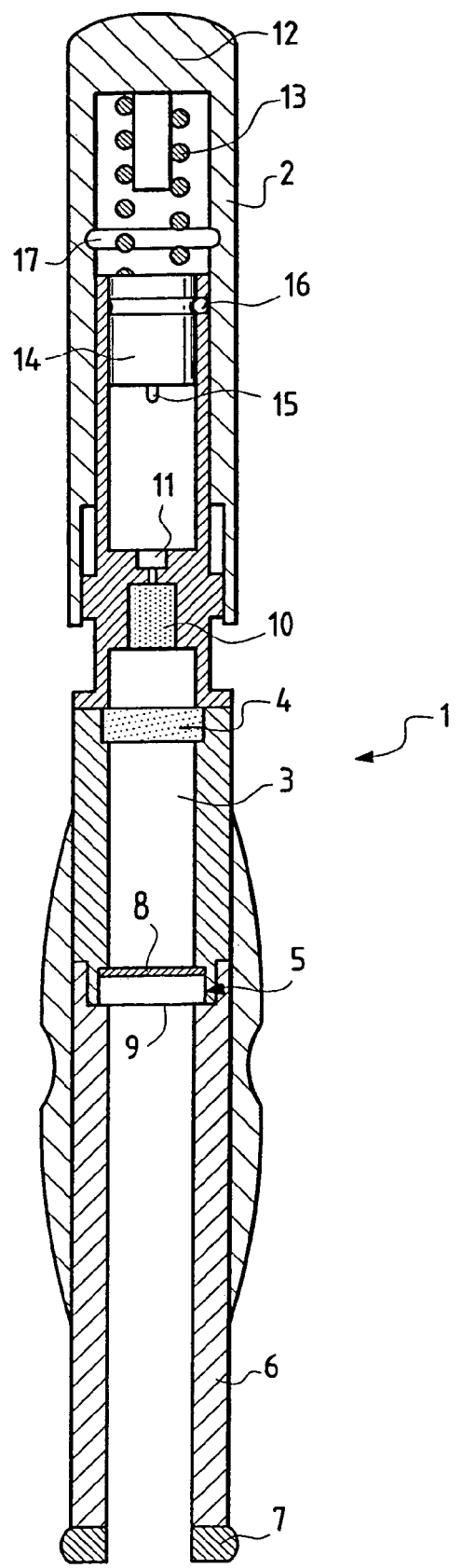
FIG. 1 is a longitudinal cross section through a needleless syringe according to the invention, for which the diameters of the expansion chamber and of the ejection tube are identical.

Referring to FIG. 1, a needleless syringe 1 according to the invention comprises, in succession, a pyrotechnic gas generator 2, an expansion chamber 3 equipped with a filter 4, a system 5 for retention of the particles, and the tube 6 used for ejection of said particles and intended to bear against the skin of the patient who is to be treated.

This bearing position can preferably be facilitated by means of a shock-absorbing rim 7 situated at the end of said tube 6. The gas expansion chamber 3 and the internal channel of the ejection tube 6 are of substantially cylindrical shape and both have the same diameter. The system 5 for retention of the particles, which marks the boundary between the chamber 3 and the tube 6, is made up of a burstable protective seal 8 and a thin membrane 9 placed downstream of said protective seal, these two elements being parallel to one another, in a position transverse with respect to the axis of the tube 6 and are both fixed to said tube 6. The particles of active principle occupy the space delimited by these two elements, with a rate of compaction preferably of between 1% and 70%.

According to a preferred embodiment of the invention, the length of the chamber 3 is 3.5 cm, the length of the ejection tube 6 as 8.5 cm, and their diameter is 0.8 cm. The burstable protective seal, which is situated on the side toward the expansion chamber 3, is calibrated in order to burst at a dynamic pressure at least equal to 70 bar, and the membrane 9 for its part serves exclusively to hold the particles in place, without presenting the slightest form of resistance to the gases which are produced.

Said membrane 9 is advantageously thin and nonelastic and, like the protective seal 8, it has lines of weakening defining a starshaped pattern so that it can open out like petals, without risking breaking open in a disorderly manner which could produce undesired fragments.

According to another embodiment, the membrane 9 can be replaced by a transverse grille which is likewise fixed to the inside of the tube 6 and contains, inserted within its interstices, the particles of active principle. In relation to the direction of propagation of the gases emitted, the protective seal 8 remains upstream of said grille.

At its end nearest to the pyrotechnic gas generator 2, the expansion chamber 3 has a transverse filter 4 which is intended, on the one hand, to trap certain solid particles generated by the combustion and, on the other hand, to cool the gases before they enter said chamber 3. Said filter 4 advantageously consists of a stack of metal grilles with an ever closer pitch and ending in a sheet of ceramic paper.

This filter 4 ensures that the temperature of the gases does not exceed 1500 K in the expansion chamber 3, so as not to damage the particles of active principle arranged in their seat. The pyrotechnic gas generator 2 comprises a device for initiating the pyrotechnic charge 10 and involving a percussion device and a primer 11. The percussion device, which is triggered by a push button 12, comprises a spring 13 and a weight 14 equipped with a striker 15. The weight 14 is blocked by at least one ball 16 wedged between said weight 14 and the push button 12, and said push button 12 has a circular inner groove 17.

Figure 2:
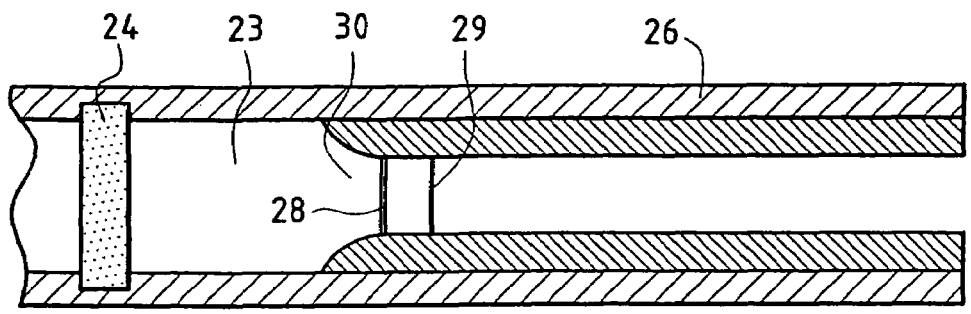
FIG. 2 is a diagram, in longitudinal cross section, of an expansion chamber having a zone of narrowing continued by a straight cylindrical ejection tube.

Referring to FIG. 2, according to a second preferred embodiment of the invention, the needleless syringe comprises, in succession, a pyrotechnic gas generator (not shown in the figure), a gas expansion chamber 23, a means for retention of the particles, likewise consisting of a burstable protective seal 28 and a membrane 29 placed downstream of said protective seal 28, and a tube 26 for ejection of said particles. The chamber 23 has a filter 24 having the same functions as those described for the first preferred embodiment of the invention, namely trapping of the undesirable solid particles and cooling of the gases of combustion.

According to this preferred embodiment of the invention, the syringe has the same pyrotechnic gas generator as that described succinctly for the first preferred embodiment of the invention. The main difference from the first embodiment described hereinabove lies in the fact that the ejection tube 26 has a smaller internal diameter, smaller than that of the expansion chamber 23. More precisely, the expansion chamber 23 has a substantially cylindrical shape continued by a zone of progressive narrowing 30 which opens into the ejection tube 26.

The system for retention of the particles is situated in said tube 26 just at the outlet of the zone of narrowing 30 from the chamber 23 corresponding to the place where the tube 26 begins to have a constant cross section.

The sum of the lengths of the chamber 23 and of the tube 26 is preferably 10 cm, and the diameters of the chamber 23 and of the tube 26 are 1.2 cm and 0.8 cm, respectively. The zone of narrowing 30 preferably has the form of a convergent nozzle and its length is 0.6 cm. For a given pyrotechnic gas generator, the configuration in which the cross section of the tube 26 is smaller than that of the chamber 23 is more effective, in terms of speed of emission of particles of active principle, than that in which the chamber 3 and the tube 6 are in continuity with one another with the same diameter.

Figure 3:
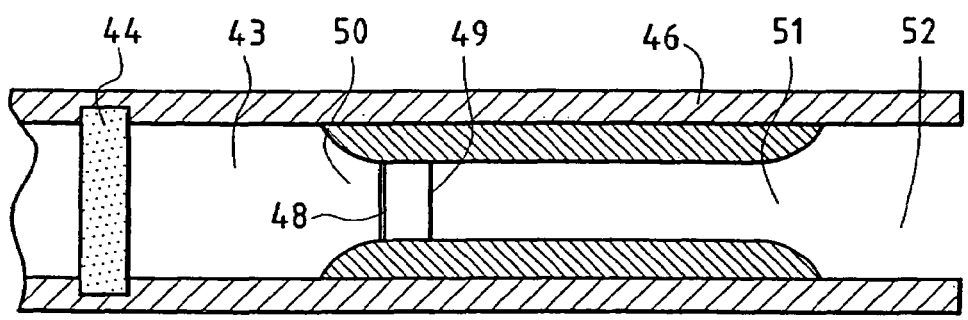
FIG. 3 is a diagram, in longitudinal cross section, of an expansion chamber similar to that in FIG. 2, for which the ejection tube has a divergent end part.

Referring to FIG. 3, according to a third preferred embodiment of the invention, the needleless syringe comprises, in succession, a pyrotechnic gas generator (not shown in the figure), a gas expansion chamber 43, a means for retention of the particles, likewise consisting of a burstable protective seal 48 and a membrane 49, and a tube 46 for ejection of said particles. The chamber 43 has a filter 44 which has the same functions as those described above. The ejection tube 46 has a reduced diameter smaller than that of the expansion chamber 43, said chamber 43 having a substantially cylindrical shape continued by a zone of progressive narrowing 50 which opens into the ejection tube 46. The system for retention of the particles is situated at the same location as that specified in the description of the second preferred embodiment of the invention. The fundamental difference compared with the second preferred embodiment of the invention is that the downstream segment of the tube 46 via which the particles are ejected has a divergent conical part 51 continued via a straight cylindrical part 52 whose free end comes into contact with the skin of the patient who is to be treated. This widening at the end constitutes a vent for the overpressure produced in the tube 46 and its main function is to disperse the residual pressure at the outlet of the syringe in such a way as to reduce any undesirable effect which could be harmful to the patient. This drop in pressure has practically no influence on the speed of the particles at the moment they impact the skin.

The dimensional characteristics of the second embodiment of the invention are retained for this third embodiment, and it will be noted here that the length of the divergent conical zone 51 of the tube 46 is approximately 0.8 cm.

The operating principle of a needleless syringe according to the invention, involves the following steps.

The user positions the syringe 1 in such a way that the end of the ejection tube 6, 26, 46 comes to bear against the skin of the patient who is to be treated. Pressing on the push button 12 causes it to slide along the syringe until the groove 17 comes level with the ball 16 blocking the weight 14. A spring 13 placed in the syringe 1 offers a certain degree of resistance to the push button 12 so that the user has to exert a particular force in order to depress said button 12. As the ball 16 is no longer wedged in place, it frees the weight 14 which, under the effect of the spring 13 which releases, is propelled toward the primer 11, with the striker 15 leading.

The primer 11 which is then initiated causes firing of the pyrotechnic charge 10. The combustion gases first pass through a filter 4, 24, 44 which holds back some of their particles and cools them, then the gases accumulate in the expansion chamber 3, 23, 43 until they reach a threshold pressure situated at around 70 bar.

The protective seal 8, 28, 48 ruptures abruptly, creating a shock wave whose front accelerates the particles of active principle just held back by a nonresistant membrane 9, 29, 49. The solid particles of active principle are thus accelerated in the ejection tube 6, 26, 26 before impacting the skin of the patient who is to be treated.

What is claimed is:

1. A needleless syringe (1) comprising, in succession, a gas generator, a gas expansion chamber (3, 23, 43), a means for retention of the particles of an active principle, and a tube (6, 26, 46) for ejection of said particles, characterized in that the gas generator is a pyrotechnic generator (2) comprising a pyrotechnic charge (10) which generates gas, and an initiation device, and in that the retention means comprises at least one protective seal (8, 28, 48) which is fixed to the ejection tube (6, 26, 46) and is intended to burst under the effect of the gases produced by the combustion of said charge (10).

2. The needleless syringe as claimed in claim 1, characterized in that the pyrotechnic charge (10) is a low-oxygenation propellant producing gases whose temperature is below 1900 K.

3. The needleless syringe as claimed in claim 1, characterized in that the protective seal (8, 28, 48) is calibrated to yield at a dynamic pressure of at least 70 bar in the chamber (3, 23, 24).

4. The needleless syringe as claimed in claim 1, characterized in that the expansion chamber (3, 23, 43) comprises a filter (4, 24, 44).

5. The needleless syringe as claimed in claim 1, characterized in that the maximum temperature reached in the expansion chamber (3, 23, 43) is between 350 K and 1500 K.

6. The needleless syringe as claimed in claim 1, characterized in that the ejection tube (6) is a straight cylinder.

7. The needleless syringe as claimed in claim 6, characterized in that the gas expansion chamber (3) is substantially cylindrical and its internal diameter is close to that of the ejection tube (6).

8. The needleless syringe as claimed in claim 7, characterized in that the ratio of the sum of the lengths of the chamber (3) and of the tube (6) to their diameter is between 3 and 25.

9. The needleless syringe as claimed in claim 7, characterized in that the ration of the length of the tube (6, 26, 46) to the length of the chamber (3, 23, 43) is between 1 and 5 and the sum of these two lengths is between 8 cm and 15 cm.

10. The needleless syringe as claimed in claim 6, characterized in that the expansion chamber (23) has a substantially cylindrical shape continued via a zone of narrowing (30) which opens into the ejection tube (26), such that the internal diameter of said tube (26) is smaller than the internal diameter of the cylindrical part of said chamber (23) and the protective seal (28) is fixed in the ejection tube (26) of reduced diameter.

11. The needleless syringe as claimed in claim 10, characterized in that the zone of narrowing (30) is progressive, having a convergent nozzle shape.

12. The needleless syringe as claimed in claim 10, characterized in that the ratio of the diameter of the cylindrical part of the expansion chamber (23) to the internal diameter of the ejection tube (26) is between 1.1 and 3.

13. The needleless syringe as claimed in claim 10, characterized in that the downstream segment of the tube (46), through which the particles are ejected, has a divergent conical part (51) continued by a straight cylindrical part (52) whose free end comes into contact with the skin.

14. The needleless syringe as claimed in claim 7, characterized in that the diameter of the particles of active principle is between 20 $\mu$m and 100 $\mu$m, and the total mass of said active principle is between 1 mg and 10 mg.

15. The needleless syringe as claimed in claim 1, characterized in that the particles are lodged between the protective seal (8, 28, 48) and a membrane (9, 29, 49) placed downstream of said protective seal (8, 28, 48) in relation to the direction of propagation of the gases.

16. The needleless syringe as claimed in claim 15, characterized in that the compaction of the particles is between 1% and 70%.

17. The needleless syringe as claimed in claim 1, characterized in that the density of the particles is between 1 and 22.

18. The needleless syringe as claimed in claim 1, characterized in that the ratio of the mass of the pyrotechnic charge (10) to the mass of the active principle to be ejected is between 1 and 50.

19. The needleless syringe as claimed in claim 1, characterized in that the means for retention of the particles comprises a transverse grille which is fixed to the ejection tube and on which said particles are maintained, these particles being able to be ejected under the effect of the pressure of the gases generated by the combustion of the pyrotechnic charge.

20. The needleless syringe as claimed in claim 1, characterized in that the device for initiation of the pyrotechnic charge (10) comprises a percussion device and a primer (11).

* * * * *